United States Patent [19]

DeWald et al.

[11] Patent Number: 5,298,578

[45] Date of Patent: * Mar. 29, 1994

[54] USE OF PHENOTHIAZINE DERIVATIVES TO INHIBIT SCALE BUILD UP DURING POLYMERIZATION OF VINYL CHLORIDE

[75] Inventors: Raymond C. DeWald, Douglassville; Paul O. Hong, Wayne, both of Pa.

[73] Assignee: Occidental Chemical Corporation, Niagara Falls, N.Y.

[*] Notice: The portion of the term of this patent subsequent to Aug. 1, 2006 has been disclaimed.

[21] Appl. No.: 424,415

[22] Filed: Oct. 20, 1989

Related U.S. Application Data

[63] Continuation-in-part of Ser. No. 344,169, Feb. 16, 1989, Pat. No. 4,960,885, which is a continuation-in-part of Ser. No. 79,315, Jul. 30, 1987, Pat. No. 4,855,424.

[51] Int. Cl.5 ............................................. C08F 2/16
[52] U.S. Cl. .................................... 526/74; 526/62
[58] Field of Search ........................................ 526/74

[56] References Cited

U.S. PATENT DOCUMENTS

| | | |
|---|---|---|
| 2,415,252 | 2/1947 | Levi . |
| 2,528,092 | 10/1950 | Smith et al. . |
| 2,981,722 | 4/1961 | Enk et al. . |
| 3,997,707 | 12/1976 | Aruga ................... 526/192 |
| 4,180,634 | 12/1979 | Koyanagi ............... 526/238 |
| 4,229,510 | 10/1980 | Watarai et al. . |
| 4,377,672 | 3/1983 | Geschonke et al. . |
| 4,465,881 | 8/1984 | Miller et al. . |
| 4,528,337 | 7/1985 | Kreilein et al. . |
| 4,529,500 | 7/1985 | Miller et al. . |
| 4,565,834 | 1/1986 | Buysch et al. . |
| 4,845,174 | 7/1989 | Amano ................... 526/62 |
| 4,853,446 | 8/1989 | DeWald ................. 526/205 |
| 4,855,424 | 8/1989 | Hong et al. . |

OTHER PUBLICATIONS

Chemical Abstracts (1983) vol. 98:144251d, Romanovich et al.

*Primary Examiner*—Christopher Henderson
*Attorney, Agent, or Firm*—Wayne A. Jones; Richard D. Fuerle

[57] ABSTRACT

Polyvinyl chloride reactor wall scale is reduced by conducting the polymerization in the presence of a phenothiazine dimer or higher oligomer made by reacting an aldehyde such as acetaldehyde or benzaldehyde with phenothiazine, or by reacting 2-acetylphenothiazine with formaldehyde.

6 Claims, No Drawings

USE OF PHENOTHIAZINE DERIVATIVES TO INHIBIT SCALE BUILD UP DURING POLYMERIZATION OF VINYL CHLORIDE

This is a continuation-in-part of application Ser. No. 344,169, filed Feb. 16, 1989, now U.S. Pat. No. 4,960,885, which was a continuation-in-part of application Serial No. 079,315, filed Jul. 30, 1987, now U.S. Pat. No. 4,855,424.

CONTINUATION DATA TO RELATED APPLICATIONS

The application Ser. No. 213,743, filed Jun. 30, 1988, now U.S. Pat. No. 4,853,446 is also a continuation-in-part of Ser. No. 079,315 now U.S. Pat. No. 4,855,424.

BACKGROUND OF INVENTION AND INFORMATION DISCLOSURE STATEMENT

1. Field of Invention

U.S. Pat. Nos. 4,853,446 and 4,855,424 disclose and claim novel compounds and compositions which have been found to inhibit the build-up of scale on the walls of vinyl chloride polymerization reactors. Such reactor scale interferes with heat transfer, and consumes valuable monomer which is lost to the final products, and results in the increase in waste product that must be disposed of safely.

The above listed patents disclose the use of the additive of the invention in various polymerization reactions for making polyvinyl chloride including emulsion polymerization, bulk or mass polymerization, suspension polymerization and microsuspension polymerization.

Copending application Ser. No. 07/424,435 filed on even date herewith, discloses and claims the use of the compounds and compositions disclosed in the foregoing patents in a microsuspension process wherein the polymerization is conducted in a tubular reaction zone without agitation. The disclosure of this copending application is incorporated herein by reference. The latter microsuspension process is disclosed and claimed in U.S. Pat. Nos. 2,981,722; 4,377,672 and 4,528,327, the disclosures of which are incorporated by reference. In this process, the tubular reactor is preferentially vertically elongated and preferably has a substantially circular cross-section.

The purpose of this invention is to provide improved polyvinyl chloride polymerization processes that utilize certain phenothiazine derivatives to reduce reactor wall fouling or scale deposits, as well as flocculated material during polymerization of vinyl chloride and comonomers.

2. Prior Art

U.S. Pat. No. 2,415,252 describes the preparation of phenothiazine derivatives by reacting phenothiazine with formaldehyde and an alcohol under conditions that produce a modified phenothiazine that has attached thereto a methylene group and an alkoxy group. The compounds and their solutions in oil are said to be useful for pharmaceutical, veterinary and pest-control purposes.

U.S. Pat. No. 2,528,092 describes the reaction of phenothiazine with formaldehyde and N-dimethylaniline. The resulting compound is useful as an antioxidant for mineral oil lubricants.

U.S. Pat. No. 4,465,881 describes N,N'-dimers of phenothiazine or a substituted phenothiazine. The compounds result from the linkage of two phenuchiazine molecules through their N groups. These dimers are prepared by heating phenothiazine in the presence of an organic peroxide. These dimers are disclosed to be useful to stabilize vinyl aromatic compounds such as styrene and substituted styrenes against undesired polymerization.

U.S. Pat. No. 4,529,500 discloses the use of the N,N'-dimer of phenothiazine or a substituted phenothiazine to protect hydrocarbon processing equipment against fouling during the processing of hydrocarbons at elevated temperatures.

An article published in the U.S.S.R. by Romanovich and co-authors and reported in Chemical Abstracts as 98:144251d, describes the reaction of phenothiazine and formaldehyde under conditions that favor the production of hardened products, wherein reaction appears to take place at the nitrogen group of the phenothiazine, ultimately resulting in the formation of cross-linked products of relatively high molecular weight.

In U.S. Pat. No 4,229,510, a polymer material is formed from a substituted phenothiazine wherein the nitrogen group is substituted with an alkyl group. It appears that reaction with formaldehyde occurs between the phenyl groups and formaldehyde. The resulting product has the nitrogen group blocked with the alkyl group of the starting material. The resulting products are reported to have photoconductive properties.

U.S. Pat. No. 4,565,834 describes compounds that have the formula of a dimer or polymer of phenothiazine. The patentees' compositions are useful as stabilizer-containing reactive components for the production of polyurethane foams which have little or no tendency toward core decolorization.

SUMMARY OF THE INVENTION

The purposes of this invention are accomplished by providing polymerization processes for polymerizing vinyl chloride and co-monomers to polyvinyl chloride and co-polymers, which comprises conducting the polymerization in the presence of a compound having the formula

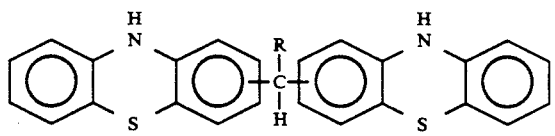

wherein R is —CH₃ or

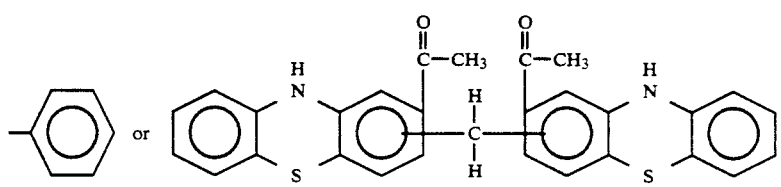

The purposes of this invention are also accomplished by providing polymerization processes for polymerizing vinyl chloride and co-monomers to polyvinyl chloride and co-polymers which comprises conducting the polymerization in the presence of a composition having the formula

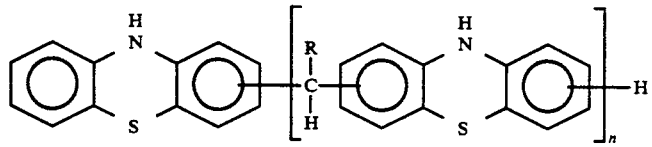

wherein n has an average value of about one to about five, and wherein R is —CH₃ or

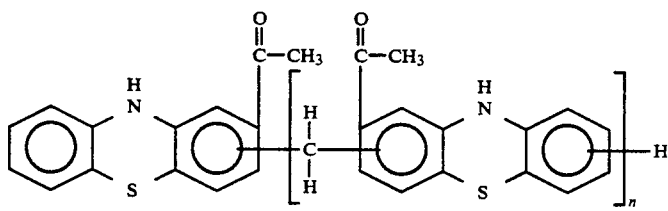

wherein n has an average value of about one to about five.

The polymerization processes of the invention include emulsion polymerization, bulk or mass polymerization, suspension polymerization and microsuspension polymerization.

The invention also includes the process of reacting phenothiazine with selected aldehydes such as acetaldehyde and benzaldehyde.

The invention further includes the process of reacting a substituted phenothiazine with formaldehyde. A suitable substituted phenothiazine is acetylphenothiazine.

In the foregoing processes, the phenothiazines are reacted with the aldehydes in the presence of a liquid diluent that is a solvent for the phenothiazine, but a non-solvent for the dimer of phenothiazine and an aldehyde and higher oligomers of phenothiazine and an aldehyde.

These reaction processes are generally conducted in the presence of a strong acid catalyst. The aldehyde is added slowly to the reaction mixture over the course of the reaction. The product can be filtered and dried.

EMBODIMENTS OF THE INVENTION

The invention involves reaction products of the compound phenothiazine which has the formula

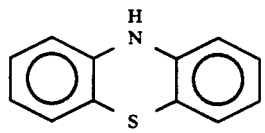

This compound is currently used in animal disease control, in pharmaceutical applications, such as against pinworms in animals.

Also useful in preparing the compounds and compositions of the invention is the compound 2-acetylphenothiazine,

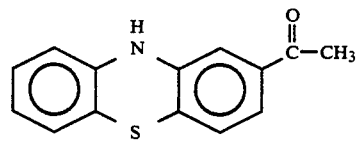

In the preparation of the compositions of the invention, the phenothiazine is reacted with an aldehyde. The molar ratio of aldehyde to phenothiazine is generally in the range of about 0.1 to less than 1, preferably in the range of about 0.4 to less than 1, and more preferably about 0.5.

Diluents for the reaction mixture of the invention are liquids that dissolve the phenothiazine, but which are not solvents for the dimer of the phenothiazine and the aldehyde and higher oligomers of the phenothiazine and the aldehyde. Thus, in the course of the reaction, as the dimer and higher oligomers of the phenothiazine are formed, such dimers and higher oligomers precipitate from the diluent and can be removed from the reaction mixture.

Suitable diluents include non-polar solvents such as tetrahydrofuran (THF), dimethylformamide (DMF), cyclohexanone and dimethylsulfoxide (DMSO).

Suitable polar diluents include alcohols, preferably those alcohols having one to five carbon atoms, although higher alcohols up to 10 carbons can be used. Suitable alcohols include methanol, ethanol, n-propanol, isopropanol, n-butanol, secondary butanol, isobutanol and tert-butanol.

With respect to the reactions of the invention, polar solvents are preferred, but mixtures of polar and nonpolar solvents are also found to be suitable to perform the function of dissolving the monomer but precipitating the dimer and higher oligomers. When the mixtures are used, the weight ratio of non-polar to polar solvent is generally in the range of about 0.1 to 10, preferably about 0.5 to 2, and still more preferably about 1 to 1. It is found that the solubility function is important in determining the structure of the product of the invention. Thus, if too powerful a solvent is employed, the dimer and higher oligomers do not precipitate and too high a molecular weight is achieved. If, on the other hand, the solvent is too poor, the monomer has difficulty dissolving and being available for the reaction with the formaldehyde to form the reaction product.

The diluent is employed in the reaction mixture such that the phenothiazine is present in an amount from about one or two weight percent up to about 25 weight percent, preferably up to about 10 weight percent of the diluent. The reaction product should be sufficiently dilute so that it can be filtered to remove the solvent from the product.

Either acidic or alkaline compounds can be employed as catalysts for the reaction. However, acid compounds are preferred, and of these the strong acids are more preferred. The preferred compounds include hydrochloric acid, sulfuric acid, nitric acid and phosphoric acid. Suitable caustic compounds include sodium hydroxide and other alkali metal hydroxides.

In the process of the invention, the aldehyde is slowly added to the mixture of diluent and phenothiazine so that there is an orderly reaction to form the dimer and higher oligomers, and subsequent precipitation of the dimers and oligomers from the reaction mixture.

The preferred reaction temperature is in the range of room temperature to the reflux temperature of the lowest boiling diluent, preferably about 60 to 80 degrees Celsius.

The reaction mixture is removed from the reaction vessel and filtered by conventional means. Suitable filter media include paper and cloth, such as nylon cloth.

The filtered product is dried at a temperature in the range of about room temperature up to the melting point of the composition of the invention, preferably at a temperature of about 50 to 100 degrees Celsius.

The reaction product of the invention generally comprises a mixture of the following components.

| Component | Weight Percent |
| --- | --- |
| Phenothiazine Monomer | 1 to 10 |
| Dimer | 70 to 85 |
| Trimer | 5 to 15 |
| Higher Oligomers | 5 to 10 |

The reaction product generally has the formula

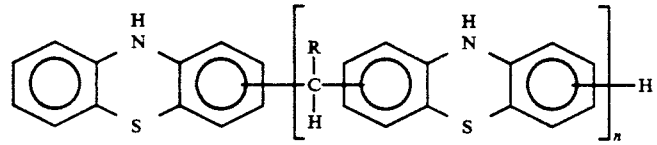

wherein R is —CH$_3$ or

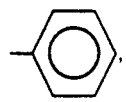

and wherein n has an average value of about 1 to about 5, preferably 1 to about 2, and more preferably 1 to about 1.5. The composition is composed of a mixture of individual compounds of the formula wherein n is an integer from 1 to about 10, preferably from 1 to about 5.

An alternative reaction product has the formula

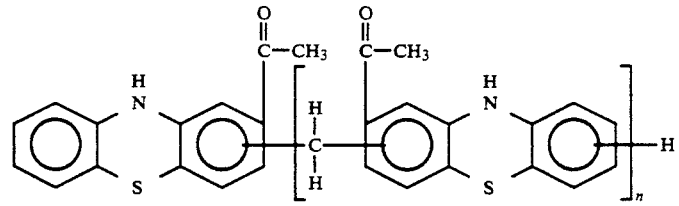

wherein n has an average value of about 1 to about 5 preferably 1 to about 2, and more preferably 1 to about 1.5. The composition is composed of a mixture of individual compounds of the formula wherein n is an integer from 1 to about 10, preferably from 1 to about 5.

The reaction mixture can be processed to change the relative ratios of the foregoing components. Thus, the unreacted monomer can be removed from the reaction mixture by methanol extraction down to about 0.5 weight percent or less of unreacted monomer.

The dimer can be separated from the trimer and higher oligomer materials by a series of extractions with suitable solvents.

The conversion of the phenothiazine to dimer and higher oligomer is generally in the range of about 75 to 90 percent.

The dimer of the invention or the reaction products including the dimer are utilized as follows in the reduction or elimination of scale and flocculated material in a reaction vessel and components such as an agitator used for the polymerization of vinyl chloride. The compositions of the invention are also useful in the polymerization of vinyl chloride with α-olefinically unsaturated comonomers, more specifically, ethylenically unsaturated comonomers in a proportion of up to about 80 mole percent comonomers, more specifically, up to about 40 mole percent comonomers. Such comonomers include vinyl acetate, and other ethylenically unsaturated monomers that are well known in the art.

The dimer alone or together with higher oligomers is dissolved in a suitable solvent such as tetrahydrofuran (THF) in a proportion of about 0.3 to about 1 weight percent. The resulting solutions are then brushed or sprayed on the reactor walls, on the reactor agitator, and inside the reactor head. The polymerization reaction mixture is inhibited from forming undesirable scale on the reactor components. Other solvents that can be employed in the application of the solutions to the reactor components include dimethylformamide (DMF), cyclohexanone and dimethylsulfoxide (DMSO).

The composition of the invention can also be added directly to the polymerization reaction mixture, generally in a proportion of about 0.0001 to about 0.01 weight percent solids, preferably about 0.001 weight percent solids based on the weight of vinyl chloride and comonomers. The composition of the invention can be added to the polymerization zone as dry solid or in solution in the foregoing solvents. The composition can also be added in the wet cake form after filtering, but before drying in the manufacturing process.

The dimer of the invention, or the reaction products including the dimer, are also useful in inhibiting the polymerization of monomers such as vinyl chloride or in shortstopping the polymerization of such monomers.

EXAMPLES

In the following examples and throughout the specification and claims, parts are by weight and temperatures are in degrees Celsius, unless indicated otherwise.

EXAMPLE 1

(a) 10.0 grams of phenothiazine were stirred with 50 cc of 95 percent isopropanol while adding 4.0 cc of concentrated HCl and 1.5 cc of acetaldehyde. The mixture was heated with stirring at reflux for 2 hours, then filtered while hot on a Buchner funnel. The filter cake was washed with hot isopropanol to remove unreacted phenothiazine, then washed with dilute ammonium hydroxide to remove residual HCl and dried at 60° C. The tan powder was soluble in tetrahydrofuran and showed a strong secondary amine band and a 1,2,4-tri-substituted benzene ring band on the infrared curve, indicating that the acetaldehyde has reacted only with the benzene rings.

(b) A PVC microsuspension polymerization known to yield high reactor buildup was carried out at 55° C. The agitator was coated with 1 percent by weight solution in tetrahydrofuran of the product made in accordance with Example 1. The following polymerization formulation was used:

|  | Grams |
| --- | --- |
| Vinyl Chloride | 400 |
| Deionized Water | 370 |
| Sodium Lauryl Sulfate | 4.0 |
| Mixed Fatty Alcohols | 5.0 |
| Lauroyl Peroxide | 0.2 |

In order to provide conditions for high reactor buildup, homogenization of the formulation was carried out at a low pressure for 2½ minutes before polymerization.

A control polymerization was carried out with no coating on the agitator.

Buildup on all surfaces of the control reactor amounted to 8.0 grams with 5.0 grams of flocculated material. Buildup in the reactor with the agitator coated amounted to 1.2 grams with 0.9 gram of flocculated material.

EXAMPLE 2

(a) 10.0 grams of 2-acetylphenothiazine were stirred with 50 cc of 95 percent isopropanol while adding 4.0 cc of concentrated HCl and 2.5 cc of 37 percent formaldehyde. After refluxing 2 hours with stirring, the mixture was filtered while hot on a Buchner funnel. The filter cake was washed with hot isopropanol to remove unreacted starting material, then washed with dilute ammonium hydroxide to remove residual HCl and dried at 60° C. The yellow powder was soluble in tetrahydrofuran and showed an infrared spectrum similar to that of the product in Example 1, indicating that the formaldehyde has reacted only with the benzene rings.

(b) A PVC microsuspension polymerization using the same formulation and procedure as in Example 1 (b) was carried out with the agitator coated with a 1 percent by weight solution in tetrahydrofuran of the product made in accordance with Example 2(a).

Buildup on all surfaces of the reactor with the agitator coated, amounted to 0.1 gram with 1.0 gram of flocculated material.

EXAMPLE 3

(a) 10.0 grams of phenothiazine were stirred with 50 cc of 95 percent isopropanol while adding 4.0 cc concentrated HCl and 3.6 cc of benzaldehyde. The mixture was heated at reflux with stirring for 2 hours, then filtered while hot on a Buchner funnel. The filtered material was washed with isopropanol to remove unreacted benzaldehyde and phenothiazine, then washed with isopropanol containing ammonium hydroxide to neutralize residual HCl. The gray/green powder showed both a secondary amine band and a tri-substituted benzene ring band on the infrared curve.

(b) When this material was added to the polymerization used in Example 2, in the amount of 12.5 ppm (based on the weight of vinyl chloride), buildup on the metal surfaces and the glass bowl amounted to 1.2 grams together with 0.9 gram of flocculated material.

EXAMPLE 4

(a) Example 2 was repeated with diphenylamine used in place of 2-acetyl phenothiazine.

(b) When the reaction product was coated in a 1 percent tetrahydrofuran solution on the agitator, and a polymerization carried out according to Example 3, buildup on the metal surfaces and the glass bowl amounted to 3.8 grams together with 4.3 grams of flocculated material.

EXAMPLE 5

(a) Example 2 was repeated, using the tertiary amine compound, N-methyl phenothiazine, and formaldehyde.

(b) When the reaction product was coated in a 1 percent tetrahydrofuran solution on the agitator and a polymerization carried out according to Example 1, buildup on the metal surfaces and the glass bowl amounted to 10.1 grams together with 4.3 grams of flocculated material. This shows that a phenothiazine derivative without the secondary amine functionality produces a product which forms reactor buildup and flocculation comparable to that of a control with no coating on the agitator.

We claim:

1. In a microsuspension polymerization process for polymerizing vinyl chloride to polyvinyl chloride, the improvement comprising conducting the polymerization in the presence of a composition having the formula

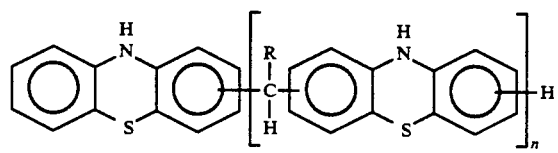

wherein n has an average value of about one to about five, and R is —CH₃ or

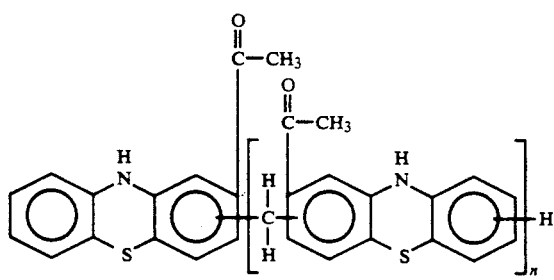

wherein n has an average value of about one to about five.

2. The process of claim 1 wherein a solution of said composition in a solvent is coated on the walls of the polymerization zone.

3. The process of claim 1 wherein said composition is added to the polymerization zone in a proportion of about 0.0001 to about 0.01 weight percent solids based on the weight of vinyl chloride and comonomers.

4. The microsuspension process of claim 1 wherein the polymerization is conducted in a tubular zone without agitation.

5. The microsuspension process of claim 2 wherein the polymerization is conducted in a tubular zone without agitation.

6. The microsuspension process of claim 3 wherein the polymerization is conducted in a tubular zone without agitation.

* * * * *